United States Patent [19]

Lunkenheimer et al.

[11] Patent Number: 5,510,364

[45] Date of Patent: Apr. 23, 1996

[54] 2-CYANOBENZIMIDAZOLES AND THEIR USE, AND NEW PRECURSORS

[75] Inventors: Winfried Lunkenheimer, Wuppertal; Heinz-Wilhelm Dehne; Ulrike Wachendorff-Neumann, both of Monheim, all of Germany

[73] Assignee: Bayer Aktiengesellschaft, Leverkusen, Germany

[21] Appl. No.: 981,035

[22] Filed: Nov. 24, 1992

[30] Foreign Application Priority Data

Dec. 4, 1991 [DE] Germany ............ 41 39 950.1

[51] Int. Cl.$^6$ .................. A01N 43/90; C07D 491/056; C07D 235/02
[52] U.S. Cl. ................ 514/395; 514/394; 548/302.1; 548/309.7
[58] Field of Search ............. 548/302.1, 309.7; 514/395, 394

[56] References Cited

U.S. PATENT DOCUMENTS

| | | | |
|---|---|---|---|
| 3,576,818 | 4/1971 | Samuel et al. | 548/309.7 |
| 3,749,734 | 7/1973 | Hannah et al. | 548/309.7 |
| 3,988,465 | 10/1976 | Röchling et al. | 514/394 |
| 4,536,502 | 8/1985 | Giraudon et al. | 514/395 |
| 4,560,693 | 12/1985 | Rainer | 514/338 |
| 4,767,444 | 8/1988 | Heywang et al. | 514/394 X |
| 4,780,473 | 10/1988 | Baillie et al. | 548/309.7 X |
| 4,995,898 | 2/1991 | Nasu et al. | |
| 5,310,747 | 6/1992 | Enomoto et al. | |

FOREIGN PATENT DOCUMENTS

| | | |
|---|---|---|
| 0087375 | 8/1983 | European Pat. Off. |
| 219192 | 4/1987 | European Pat. Off. |
| 0251012 | 1/1988 | European Pat. Off. |
| 0251014 | 1/1988 | European Pat. Off. |
| 284277 | 9/1988 | European Pat. Off. |
| 337103 | 10/1989 | European Pat. Off. |
| 365030 | 4/1990 | European Pat. Off. |
| 390506 | 10/1990 | European Pat. Off. |
| 0487286 | 5/1992 | European Pat. Off. |
| 0517476 | 12/1992 | European Pat. Off. |
| 2607811 | 6/1988 | France ............ 548/309.7 |
| 2114567 | 8/1983 | United Kingdom. |

OTHER PUBLICATIONS

Holan et al, "2-Trihalogenomethylbenzazoles," J. Chem. Soc. (C), (1967). pp. 20-28.
Abstract of JP-62-022,782 (Jan. 30, 1987).
Abstract of JP-62-195,379 (Aug. 28, 1987).
Abstract of JP 62-240,666 (Oct. 21, 1987).
Abstract of JP-63-030,472 (Feb. 9, 1988).
Abstract of JP-63-211,270 (Sep. 2, 1988).
Abstract of JP-01-308,262 (Dec. 12, 1989).

*Primary Examiner*—Patricia L. Morris
*Attorney, Agent, or Firm*—Sprung Horn Kramer & Woods

[57] ABSTRACT

New 2-cyanobenzimidazoles of the formula (I)

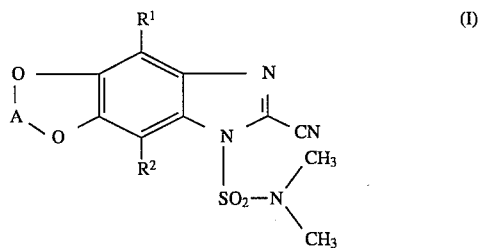

in which
$R^1$, $R^2$ and A have the meaning given in the description, a preparation process, their use in agriculture, for example against fungi, insects etc., and new intermediates.

Formula (I) provides a definition of the compounds; for example they are obtained from suitable 2-cyanobenzimidazoles which are unsubstituted in the 1-position with N,N-dimethylsulphamoyl halide. The 2-cyanobenzimidazoles which are unsubstituted in the 1-position are equally new and can be reacted from suitable phenylenediamines of the formula (IV) with methyl 2,2,2-trichloroacetimidate of the formula (V) to give the 2-trichloromethylbenzimidazoles of the formula (VI), which are equally new and from which the compounds of the formula (II) can subsequently be obtained with ammonia.

10 Claims, No Drawings

2-CYANOBENZIMIDAZOLES AND THEIR USE, AND NEW PRECURSORS

The invention relates to new 2-cyanobenzimidazoles, to a process for their preparation and to their use as pesticides, and additionally to new starting compounds.

It has been disclosed that certain 2-cyanobenzimidazoles such as, for example, the compound 5-chloro-2-cyano-1-(N,N-dimethylsulphamoyl)-benzimidazole or the compound 6-chloro-2-cyano-1-(N,N-dimethylsulphamoyl)-benzimidazole or the compound 5,6-dichloro-2-cyano-1-(N,N-dimethylsulphamoyl)-benzimidazole have fungicidal properties (compare, for example, GB 2,114,567).

However, the activity of these previously known compounds is not entirely satisfactory in all fields of application, in particular when low amounts and concentrations are applied.

New 2-cyanobenzimidazoles of the general formula (I)

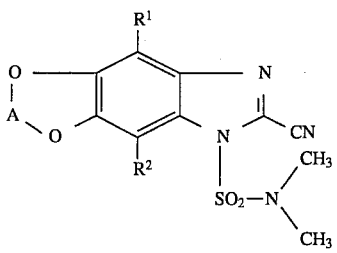

in which

R$^1$ represents hydrogen, halogen or alkyl,

R$^2$ represents hydrogen, halogen or alkyl and A represents an optionally substituted divalent alkanediyl radical, have been found.

Depending on the nature of the substituents, the compounds of the formula (I) may exist in the form of optical isomers or isomer mixtures of various compositions. The invention claims the pure isomers as well as the isomer mixtures.

Furthermore, it has been found that the new 2-cyanobenzimidazoles of the general formula (I)

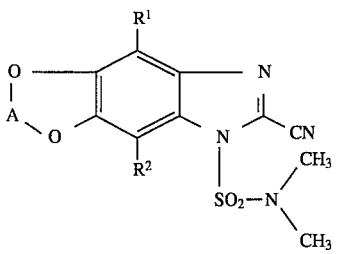

in which

R$^1$ represents hydrogen, halogen or alkyl,

R$^2$ represents hydrogen, halogen or alkyl and

A represents an optionally substituted divalent alkanediyl radical, are obtained when 2-cyanobenzimidazoles which are unsubstituted in the 1-position, of the formula (II)

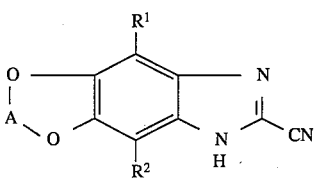

in which

R$^1$, R$^2$ and A have the abovementioned meaning, are reacted with N,N-dimethylsuphamoyl chloride, of the formula (III),

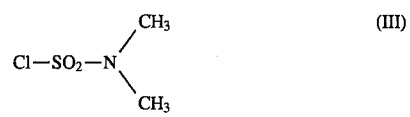

if appropriate in the presence of a diluent and if appropriate in the presence of a reaction auxiliary.

Finally, it has been found that the new 2-cyanobenzimidazoles of the general formula (I) have a good activity against pests.

Surprisingly, the 2-cyanobenzimidazoles of the general formula (I) according to the invention show a considerably better activity against phytopathogenic pathogens and against insects and mites which damage plants than the 2-cyanobenzimidazoles known from the prior art such as, for example, the compound 5-chloro-2-cyano-1-(N,N-dimethylsulphamoyl)-benzimidazole or the compound 6-chloro-2-cyano-1-(N,N-dimethylsulphamoyl)-benzimidazole or the compound 5,6-dichloro-2-cyano-(N,N-dimethylsulphamoyl)-benzimidazole, which are similar compounds chemically and from the point of view of their action.

Formula (I) provides a general definition of the 2-cyanobenzimidazoles according to the invention. Preferred compounds of the formula (I) are those in which R$^1$ represents hydrogen, fluorine, chlorine, bromine or straight-chain or branched alkyl having 1 to 4 carbon atoms, R$^2$ represents hydrogen, fluorine, chlorine, bromine or straight-chain or branched alkyl having 1 to 4 carbon atoms and A represents a divalent alkanediyl radical which has 1 to 4 carbon atoms and which is optionally monosubstituted or polysubstituted by identical or different substituents, suitable substituents being: halogen, straight-chain or branched alkyl having 1 to 6 carbon atoms, straight-chain or branched halogenoalkyl having 1 to 6 carbon atoms and 1 to 13 identical or different halogen atoms, or divalent alkanediyl having 3 to 7 carbon atoms.

Particularly preferred compounds of the formula (I) are those in which

R$^1$ represents hydrogen, chlorine, bromine or straight-chain or branched alkyl having 1 to 3 carbon atoms, R$^2$ represents hydrogen, chlorine, bromine or straight-chain or branched alkyl having 1 to 3 carbon atoms and A represents a divalent alkanediyl radical which has 1 to 4 carbon atoms and which is optionally monosubstituted to hexasubstituted by identical or different substituents, suitable substituents being: fluorine, chlorine, bromine, straight-chain or branched alkyl having 1 to 4 carbon atoms, straight-chain or branched halogenoalkyl having 1 to 4 carbon atoms and 1 to 9 identical or different halogen atoms, or divalent alkanediyl having 3 to 7 carbon atoms.

Very particularly preferred compounds of the formula (I) are those in which

R$^1$ represents hydrogen, chlorine, bromine, methyl or ethyl,

R$^2$ represents hydrogen, chlorine, bromine, methyl or ethyl and

A represents methylene, ethylene, propylene or butylene, each of which is optionally monosubstituted to tetrasubstituted by identical or different substituents, suitable substituents in each case being: fluorine, chlorine, bromine, methyl, ethyl, n- or i-propyl, trifluoromethyl, trifluoroethyl, trifluorochloroethyl, tetrafluoroethyl, pentafluoroethyl, or in each case divalent 1,4-butanediyl, 1,5-pentanediyl or 1,6-hexanediyl.

Individual 2-cyanobenzimidazoles of the general formula (I) which may be mentioned in addition to the compounds mentioned in the preparation examples are the following:

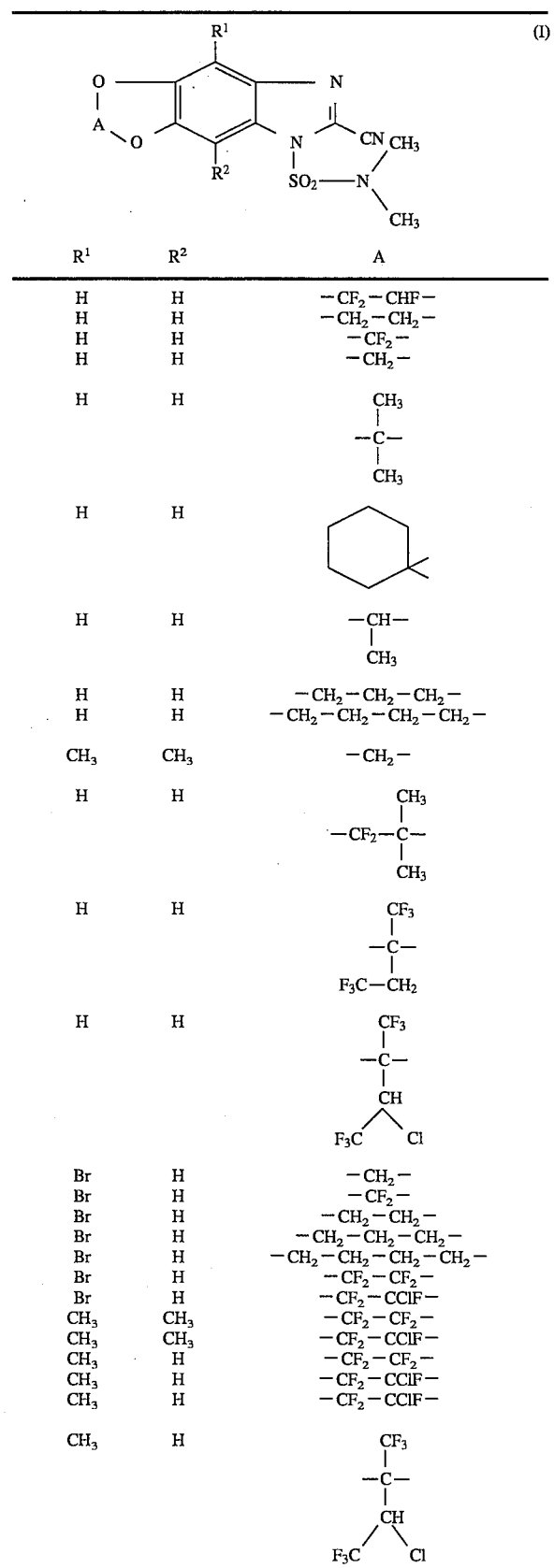

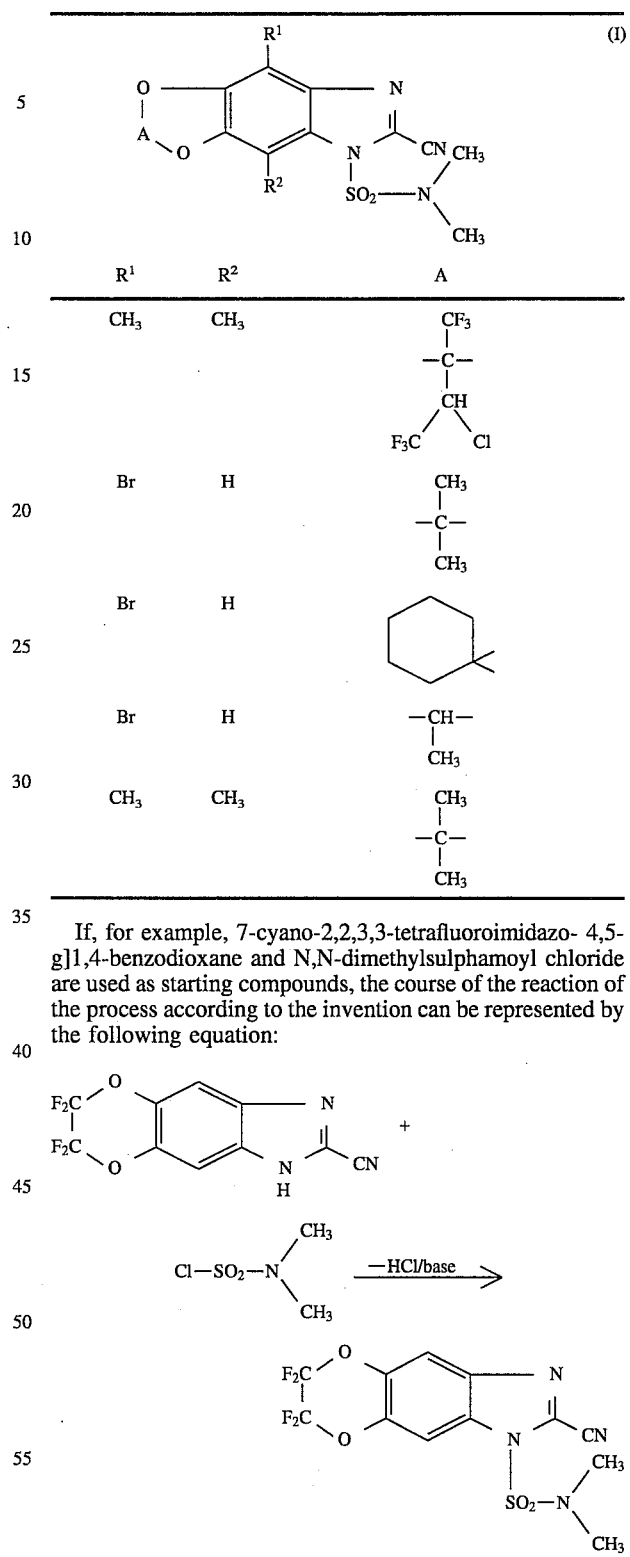

If, for example, 7-cyano-2,2,3,3-tetrafluoroimidazo- 4,5-g]1,4-benzodioxane and N,N-dimethylsulphamoyl chloride are used as starting compounds, the course of the reaction of the process according to the invention can be represented by the following equation:

Formula (II) provides a general definition of the 2-cyanobenzimidazoles which are unsubstituted in the 1-position and which are required as starting materials for carrying out the process according to the invention. In this formula (II), $R^1$, $R^2$ and A preferably represent those radicals which have already been mentioned in connection with the description of the compounds of the formula (I) according to the invention as being preferred for these substituents.

The 2-cyanobenzimidazoles which are unsubstituted in the 1-position, of the formula (II), were hitherto unknown and are equally a subject of the invention. They are obtained when phenylenediamines of the formula (IV)

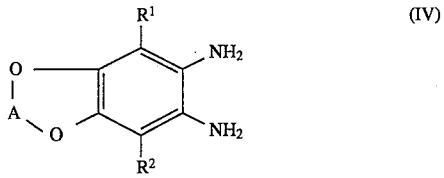

in which
R¹, R² and A have the abovementioned meaning or acid addition salts thereof are first reacted, in a first step, with methyl 2,2,2-trichloroacetimidate, of the formula (V),

at temperatures between 0° C. and 60° C., if appropriate in the presence of a diluent such as, for example, glacial acetic acid or methanol (compare, in this context, for example J. Chem. Soc. C; 1967, 20 or U.S. Pat. No. 3,576,818 [1967]) and the resulting 2-trichloromethylbenzimidazoles of the formula (VI)

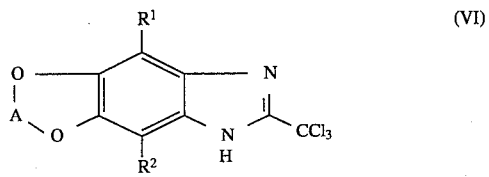

in which
R¹, R² and A have the abovementioned meaning, are then reacted, in a subsequent second step, with ammonia at temperatures between 0° C. and 60° C., if appropriate in the presence of a diluent such as, for example, methanol or water (compare, in this context, for example J. Chem. Soc. C; 1967, 25 or U.S. Pat. No. 3,576,818 [1967]).

2-Trichloromethyl-benzimidazoles of the formula (VI) were hitherto unknown and are equally a subject of the present invention.

Phenylenediamides of the formula (IV) are known or can be obtained analogously to generally known processes (compare, in this context, for example DE 3,621,301; DE 3,605,977 or DE 3,132,613).

Suitable diluents for carrying out the process according to the invention are inert organic solvents. These include, in particular, aliphatic, alicyclic or aromatic, optionally halogenated hydrocarbons such as, for example, benzine, benzene, toluene, xylene, chlorobenzene, dichlorobenzene, petroleum ether, hexane, cyclohexane, dichloromethane, chloroform or carbon tetrachloride; ethers such as diethyl ether, diisopropyl ether, dioxane, tetrahydrofuran or ethylene glycol dimethyl ether or ethylene glycol diethyl ether; ketones such as acetone or butanone or methyl isobutyl ketone; nitriles such as acetonitrile, propionitrile or benzonitrile, or esters such as methyl acetate or ethyl acetate.

The process according to the invention is preferably carried out in the presence of a suitable reaction auxiliary. Suitable reaction auxiliaries are all customary inorganic or organic bases. These include, for example, alkaline earth metal hydroxides or alkali metal hydroxides such as sodium hydroxide, calcium hydroxide, potassium hydroxide or else ammonium hydroxide, alkali metal carbonates such as sodium carbonate, potassium carbonate, potassium hydrogen carbonate, sodium hydrogen carbonate, alkali metal acetates or alkaline earth metal acetates such as sodium acetate, potassium acetate, calcium acetate as well as tertiary amines such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU).

When carrying out the process according to the invention, the reaction temperatures can be varied within a substantial range. In general, the process is carried out at temperatures between 0° C. and 150° C., preferably at temperatures between 20° C. and 120° C.

The process according to the invention is customarily carried out under atmospheric pressure. However, it is also possible to carry out the process under increased or reduced pressure.

For carrying out the process according to the invention, 1.0 to 2.0 mol, preferably 1.0 to 1.3 mol, of N,N-dimethylsulphamoyl chloride of the formula (III) and, if appropriate, 1.0 to 2.0 mol, preferably 1.0 to 1.3 mol, of a reaction auxiliary are generally employed per mole of 2-cyanobenzimidazole which is unsubstituted in the 1-position of the formula (II). The reaction is carried out and the reaction products are worked up and isolated by known processes (compare also the preparation examples).

The end products of the formula (I) are purified with the aid of customary processes, for example by column chromatography or by recrystallization. They are characterized with the aid of the melting point and proton nuclear resonance spectroscopy (¹H NMR).

The active compounds according to the invention have a powerful action against pests and can be employed in practice for combating undesired harmful organisms. The active compounds are suitable for use as plant protection agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some pathogens causing fungal diseases which come under the generic names listed above may be mentioned as examples, but not by way of limitation:

Pythium species, such as *Pythium ultimum;*

Phytophthora species, such as *Phytophthora infestans;*
Pseudoperonospora species, such as *Pseudoperonospora humuli* or *Pseudoperonospora cubensis;*

Plasmopara species, such as *Plasmopara viticola;*

Peronospora species, such as *Peronospora pisi* or *Peronospora brassicae;*

Erysiphe species, such as *Erysiphe graminis;*

Sphaerotheca species, such as *Sphaerotheca fuliginea;*

Podosphaera species, such as *Podosphaera leucotricha;*

Venturia species, such as *Venturia inaequalis;*

Pyrenophora species, such as *Pyrenophora teres* or *P. graminea* (conidia form: Drechslera, syn: Helminthosporium);

Cochliobolus species, such as *Cochliobolus sativus* (conidia form: Drechslera, syn: Helminthosporium);

Uromyces species, such as *Uromyces appendiculatus;*

Puccinia species, such as *Puccinia recondita;*

Tilletia species, such as *Tilletia caries;*

Ustilago species, such as *Ustilago nuda* or *Ustilago avenae;*

Pellicularia species, such as *Pellicularia sasakii;*

Pyricularia species, such as *Pyricularia oryzae*;
Fusarium species, such as *Fusarium culmorum*;
Botrytis species, such as *Botrytis cinerea*;
Septoria species, such as *Septoria nodorum*;
Leptosphaeria species, such as *Leptosphaeria nodorum*;
Cercospora species, such as *Cercospora canescens*;
Alternaria species, such as *Alternaria brassicae* and Pseudocercosporella species, such as *Pseudocercosporella herpotrichoides*.

The good toleration, by plants, of the active compounds, at the concentrations required for combating plant diseases, permits treatment of above-ground parts of plants, of vegetative propagation stock and seeds, and of the soil.

In this context, the active compounds according to the invention can be employed with particularly good success for combating diseases in fruit and vegetable growing such as, for example, against the pathogen causing tomato blight (*Phytophthora infestans*) or against the pathogen causing powdery mildew of grape vines (*Plasmopara viticola*). When used for combating these plant diseases, they show protective as well as curative properties.

Moreover, the active compounds according to the invention are suitable for combating animal pests, preferably arthropods and nematodes, in particular insects and arachnids, which occur in agriculture, in forests, in the protection of stored products and of materials, and in the hygiene field. They are effective against normally sensitive and resistant species and against all or individual development stages.

The abovementioned pests include:

From the order of the Isopoda, for example, *Oniscus asellus, Armadillidium vulgare* and *Porcellio scaber*.

From the order of the Diplopoda, for example, *Blaniulus guttulatus*.

From the order of the Chilopoda, for example, *Geophilus carpophagus* and *Scutigera spec*.

From the order of the Symphyla, for example, *Scutigerella immaculata*.

From the order of the Thysanura, for example, *Lepisma saccharina*.

From the order of the Collembola, for example, *Onychiurus armatus*.

From the order of the Orthoptera, for example, *Blatta orientalis, Periplaneta americana, Leucophaea maderae, Blattella germanica, Acheta domesticus, Gryllotalpa spp., Locusta migratoria migratorioides, Melanoplus differentialis* and *Schistocerca gregaria*.

From the order of the Dermaptera, for example, *Forficula auricularia*.

From the order of the Isoptera, for example, *Reticulitermes spp*.

From the order of the Anoplura, for example, *Phylloxera vastatrix, Pemphigus spp., Pediculus humanus corporis, Haematopinus spp.* and *Linognathus spp*.

From the order of the Mallophaga, for example, *Trichodectes spp.* and *Damalinea spp*.

From the order of the Thysanoptera, for example, *Hercinothrips femoralis* and *Thrips tabaci*.

From the order of the Heteroptera, for example, *Eurygaster spp., Dysdercus intermedius, Piesma quadrata, Cimex lectularius, Rhodnius prolixus* and *Triatoma spp*.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae, Myzus spp., Phorodon humuli, Rhopalosiphum padi, Empoasca spp., Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus spp. Psylla spp*.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria spp. Bucculatrix thurberiella, Phyllocnistis citrella, Agrotis spp., Euxoa spp., Feltia spp., Earias insulana, Heliothis spp., Spodoptera exigua, Mamestra brassicae, Panolis flammea, Prodenia litura, Spodoptera spp., Trichoplusia ni, Carpocapsa pomonella, Pieris spp., Chilo spp., Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana*.

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica spp., Psylliodes chrysocephala, Epilachna varivestis, Atomaria spp., Oryzaephilus surinamensis, Anthonomus spp., Sitophilus spp., Otiorrhynchus sulcatus, Cosmopolites sordidus, Ceuthorrhynchus assimilis, Hypera postica, Dermestes spp., Trogoderma spp., Anthrenus spp., Attagenus spp., Lyctus spp., Meligethes aeneus, Ptinus spp., Niptus hololeucus, Gibbium psylloides, Tribolium spp., Tenebrio molitor, Agriotes spp., Conoderus spp., Melolontha melolontha, Amphimallon solstitialis* and *Costelytra zealandica*.

From the order of the Hymenoptera, for example, *Diprion spp., Hoplocampa spp., Lasius spp., Monomorium pharaonis* and *Vespa spp*.

From the order of the Diptera, for example, *Aedes spp., Anopheles spp., Culex spp., Drosophila melanogaster, Musca spp., Fannia spp., Calliphora erythrocephala, Lucilia spp., Chrysomyia spp., Cuterebra spp., Gastrophilus spp., Hyppobosca spp., Stomoxys spp., Oestrus spp., Hypoderma spp., Tabanus spp., Tannia spp., Bibio hortulanus, Oscinella frit, Phorbia spp., Pegomyia hyoscyami, Ceratitis capitata, Dacus oleae* and *Tipula paludosa*.

From the order of the Siphonaptera, for example, *Xenopsylla cheopis* and *Ceratophyllus spp*.

From the order of the Arachnida, for example, *Scorpio maurus* and *Latrodectus mactans*.

From the order of the Acarina, for example, *Acarus siro, Argas spp., Ornithodoros spp., Dermanyssus gallinae, Eriophyes ribis, Phyllocoptruta oleivora, Boophilus spp., Rhipicephalus spp., Amblyomma spp., Hyalomma spp., Ixodes spp., Psoroptes spp., Chorioptes spp., Sarcoptes spp., Tarsonemus spp., Bryobia praetiosa, Panonychus spp.* and *Tetranychus spp*.

The active compounds according to the invention are distinguished by a high insecticidal activity. They can be employed with particularly good success for combating mites which are harmful to plants such as, for example, against the common spider mite (*Tetranychus urticae*). Besides, the active compounds according to the invention also show leaf-insecticidal properties.

Depending on their particular physical and/or chemical properties, the active compounds can be converted into customary formulations, such as solutions, emulsions, suspensions, powders, foams, pastes, granules, aerosols, natural and synthetic materials impregnated with active compound, very fine capsules in polymeric substances and in coating compositions for seed, and furthermore in formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is liquid solvents, liquefied gases under pressure and/or solid carriers, optionally with the use of surface-active agents, that is emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene, or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

Colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc, can be used.

The formulations in general contain between 0.1 and 95 per cent by weight of active compound, preferably between 0.5 and 90%.

When used as fungicides, the active compounds according to the invention can be present in the formulations in the form of a mixture with other known active compounds such as fungicides, insecticides, acaricides and herbicides, and in the form of mixtures with fertilizers and growth regulators.

When used as fungicides, the active compounds can be employed as such, in the form of their formulations or in the use forms prepared therefrom, such as ready-to-use solutions, suspensions, wettable powders, pastes, soluble powders, dusting agents and granules. They are applied in the customary manner, for example by watering, spraying, atomizing, scattering, dusting, foaming on, brushing on and the like. It is furthermore possible to apply the active compounds by the ultra-low-volume method or to inject the active compound preparation, or the active compound itself, into the soil. The seeds of the plants can also be treated.

In the treatment of parts of plants, the active compound concentrations in the use forms can be varied within a substantial range when used as fungicides. They are generally between 1 and 0.0001% by weight, preferably between 0.5 and 0.001%.

In the treatment of seed, amounts of active compound of 0.001 to 50 g are generally required per kilogram of seed, preferably 0.01 to 10 g, when used as fungicides.

In the treatment of the soil, active compound concentrations of 0.00001 to 0.1% by weight, preferably 0.0001 to 0.02%, are required at the site of action when used as fungicides.

When used as insecticides and acaricides, the active compounds according to the invention can be present in their commercially available formulations and in the use forms prepared from these formulations as a mixture with other active compounds such as insecticides, attractants, sterilants, acaricides, nematicides, fungicides, growth-regulating substances or herbicides. The insecticides include, for example, phosphoric acid esters, carbamates, carboxylic acid esters, chlorinated hydrocarbons, phenylureas, substances produced by microorganisms etc.

When used as insecticides and acaricides, the active compounds according to the invention can furthermore be present in their commercially available formulations and in the use forms prepared from these formulations as a mixture with synergistic agents. Synergistic agents are compounds which increase the action of the active compounds without it being necessary for the synergistic agent added to be active itself.

The active compound content of the use forms prepared with the commercially available formulations can vary within wide limits when used as insecticides and acaricides. The active compound concentration of the use forms can be from 0.0000001 to 95% by weight of active compound, preferably between 0.0001 and 1% by weight.

They are used in a customary manner appropriate for the use forms.

The preparation and the use of the active compounds according to the invention can be seen from the examples which follow.

PREPARATION EXAMPLES

Example 1

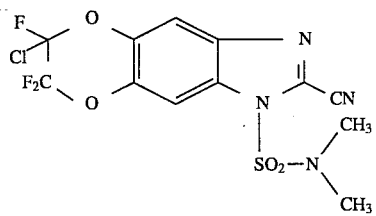

-continued

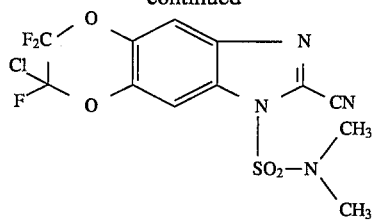

A solution of 1.6 ml (0.0165 mol) of dimethylsulphamoyl chloride in 5 ml of acetonitrile is added dropwise with stirring at room temperature to 4.4 g (0,015 mol) of racemic 2-chloro-7-cyano-2,3,3-trifluoro-imidazo[4,5-g]- 1,4-benzodioxane and 4.2 g (0.03 mol) of pulverulent potassium carbonate in 50 ml of acetonitrile, and, when the addition has ended, the mixture is refluxed for 4 hours. The mixture is subsequently cooled to room temperature and filtered, the filtrate is concentrated and the residue is partitioned between ethyl acetate (100 ml) and water (30 ml). The organic phase is washed with water, dried over sodium sulphate and freed from solvent in vacuo.

5.6 g (89% of theory) of the abovementioned mixture of melting point 160° C. to 163° C. are obtained.

PREPARATION OF THE STARTING COMPOUND Example II-1

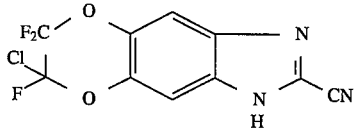

A solution of 3.2 g (0.005 mol) of racemic 2-chloro-7-trichloromethyl-2,3,3-trifluoro-imidazo[4,5-g]- 1,4-benzodioxane (60 per cent) in 10 ml of ethanol is added dropwise with stirring at room temperature to 30 ml of concentrated aqueous ammonium, and, when the addition has ended, the mixture is stirred at room temperature for a further 4 hours. For working-up, the mixture is acidified with 20 per cent strength hydrochloric acid, extracted three times with 30 ml portions of ethyl acetate, and the combined organic phases are dried and concentrated in vacuo. The residue is chromatographed over silica gel (mobile phase: cyclohexane/ethyl acetate 2:1).

1.1 g (74% of theory) of racemic 2-chloro-7-cyano-2,3,3-trifluoro-imidazo[4,5-g]1,4-benzodioxane of melting point >230° C. are obtained.

In analogous manner the following compounds of the general formula (II) are obtained:

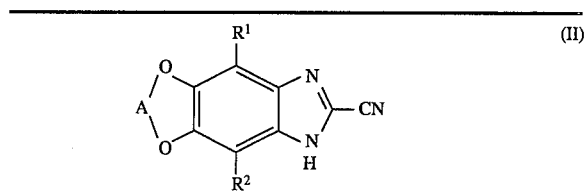

| Example No. | A | $R^1$ | $R^2$ | melting point/ °C. |
|---|---|---|---|---|
| II-3 | $-CH_2-CH_2-CH_2-$ | H | H | >230 |
| II-4 | $-CF_2-$ | H | H | >230 |
| II-5 | $-CF_2-CHF-$ | H | H | $^1$H-NMR*): 6,69 (d) |

*) The $^1$H-NMR-spectra were recorded in hexadeutero-dimethylsulfoxide (DMSO-$d_6$) using tetramethylsilane (TMS) as the internal standard. The chemical shift is given as the δ-value in ppm.

Example VI- 1

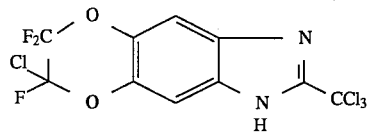

8.1 g (0,045 mol) of methyl 2,2,2-trichloroacetimidate are added dropwise with stirring at room temperature to a solution of 7.6 g (0.03 mol) of racemic 2-chloro- 6,7-diamino-2,3,3-trifluoro-1,4-benzodioxane (compare, for example, DE 3,605,977) in 60 ml of glacial acetic acid, during which process the temperature of the reaction mixture rises to 36° C., and, when the addition has ended, the mixture is stirred at room temperature for a further 20 hours. For working-up, 60 ml of water are added, the mixture is stirred for 10 minutes at room temperature, the precipitate which has separated out is filtered off with suction, washed with water and dried.

11.4 g (60% of theory) of racemic 2-chloro-7-trichloromethyl- 2,3,3-trifluoro-imidazo[4,5-g]1,4-benzodioxane (content according to HPLC approx. 60%) of melting point >230° C. are obtained.

The following compounds of the general formula (VI) are obtained in analogous manner:

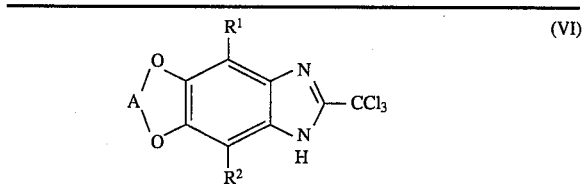

| Example No. | A | $R^1$ | $R^2$ | melting point/ °C. |
|---|---|---|---|---|
| VI-3 | $-CH_2-CH_2-CH_2-$ | H | H | >230 |
| VI-4 | $-CF_2-$ | H | H | >230 |
| VI-5 | $-CF_2-CHF-$ | H | H | 221–225 |

The following are obtained in an analogous manner and following the general preparation instructions:

Example 2

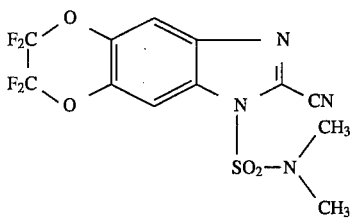

of melting point 166° C. to 170° C. and

Example 3

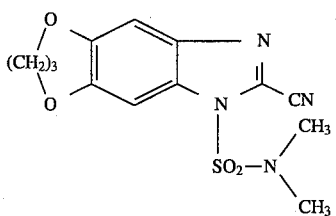

of melting point 118°–120° C.

The following 2-cyanobenzimidazoles of the general formula are obtained in an analogous manner (I)

| Example No. | A | $R^1$ | $R^2$ | melting point/ °C. |
|---|---|---|---|---|
| 4 | $-CF_2-$ | H | H | 206–208 |
| 5 | $-CF_2-CHF-$ ($-CHF-CF_2-$) | H | H | 110–114 |

Use Examples:

In the use examples which follow, the compounds listed below were employed as comparison substances:

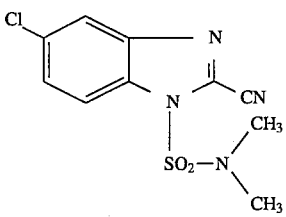  (A)

5(6)-chloro-2-cyano-1-(N,N-dimethylsulphamoyl)-benzimid-azole

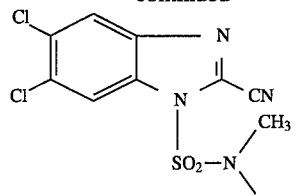  (B)

5,6-dichloro-2-cyano-1-(N,N-dimethylsulphamoyl)-benzimidazole
(both disclosed in GB 2,114,567)

Example A

Phytophthora test (tomato)/curative

Solvent: 4.7 parts by weight of acetone

Emulsifier: 0.3 parts by weight of alkylaryl polyglycol ether

To prepare a suitable preparation of active compound, 1 part by weight of active compound is mixed with the stated amounts of solvent and emulsifier, and the concentrate is diluted with water to the desired concentration.

To test for curative activity, young plants are inoculated with an aqueous spore suspension of *Phytophthora infestans*. The plants remain in an incubation cabinet for 7 hours at 20° C. and 100% relative atmospheric humidity. After a brief drying-off time, the plants are sprayed with the preparation of active compound until dripping wet.

The plants are placed in an incubation cabinet at 100% relative atmospheric humidity and approx. 20° C.

Evaluation takes place 3 days after the inoculation.

In this test, a clearly superior activity compared with the prior art is shown, for example, by the compounds of Preparation Examples: 1 and 2.

Example B

Plasmopara test (vines)/protective

Solvent: 4.7 parts by weight of acetone

Emulsifier: 0.3 parts by weight of alkylaryl polyglycol ether

To prepare a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of *Plasmopara viticola* and then remain for 1 day in a humid chamber at 20° to 22° C. and 100% relative atmospheric humidity. The plants are subsequently placed in the greenhouse for 5 days at 21° C. and approx. 90% atmospheric humidity. The plants are then moistened and placed into a humid chamber for 1 day.

Evaluation takes place 6 days after the inoculation.

In this test, a clearly superior activity compared with the prior art is shown, for example, by the compounds of Preparation Examples: 1 and 2.

Example C

Plasmopara test (vines)/curative

Solvent: 4.7 parts by weight of acetone

Emulsifier: 0.3 parts by weight of alkylaryl polyglycol ether

To prepare a suitable preparation of active compound, 1 part by weight of active compound is mixed with the stated amounts of solvent and emulsifier, and the concentrate is diluted with water to the desired concentration.

To test for curative activity, young plants are inoculated with an aqueous spore suspension of *Plasmopara viticola*. The plants remain in a humid chamber for 24 hours at 20°

C. to 22° C. and 100% relative atmospheric humidity, and, after a further 24 hours at 21° C. and 90% atmospheric humidity, the plants are sprayed with the preparation of active compound until dripping wet. The plants are subsequently placed in the greenhouse for 5 days. The plants are then moistened and placed into a humid chamber for 1 day.

Evaluation takes place 6 days after the inoculation.

In this test, a clearly superior activity compared with the prior art is shown, for example, by the compounds of Preparation Examples: 1 and 2.

Example D

Tetranychus test (OP* resistant)

*Organophosphate

Solvent: 7 parts by weight of dimethylformamide

Emulsifier: 7 part by weight of alkylaryl polyglycol ether

To prepare a suitable preparation of active compound, 1 part by weight of active compound is mixed with the stated amount of solvent and the stated amount of emulsifier, and the concentrate is diluted with emulsifier-containing water to the desired concentration.

Bean plants (Phaseolus vulgaris) which are heavily infested with all development stages of the common spider mite (Tetranychus urticae) are dipped in a preparation of active compound of the desired concentration.

After the desired period, the destruction in % is determined. 100% means that all spider mites have been killed; 0% means that no spider mites have been killed.

In this test, superior activity compared with the prior art is shown, for example, by the compounds of Preparation Examples 1 and 2.

What is claimed is:

1. A 2-cyanobenzimidazole of the formula (I)

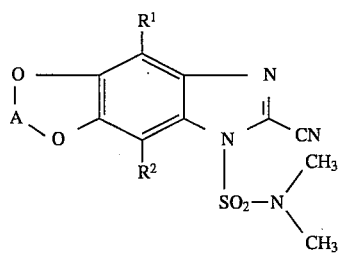

in which

R¹ represents hydrogen, halogen or alkyl,

R² represents hydrogen, halogen or alkyl and

A represents a halogen substituted divalent $C_1$–$C_4$ alkanediyl radical.

2. A 2-cyanobenzimidazole of the formula (I) according to claim 1, in which

R¹ represents hydrogen, fluorine, chlorine, bromine or straight-chain or branched alkyl having 1 to 4 carbon atoms, R² represents hydrogen, fluorine, chlorine, bromine or straight-chain or branched alkyl having 1 to 4 carbon atoms and A represents a divalent alkanediyl radical which has 1 to 4 carbon atoms and is monosubstituted or polysubstituted by identical or different substituents selected from the group consisting of halogen.

3. A 2-cyanobenzimidazole of the formula (I) according to claim 1, in which

R¹ represents hydrogen, chlorine, bromine or straight-chain or branched alkyl having 1 to 3 carbon atoms, R² represents hydrogen, chlorine, bromine or straight-chain or branched alkyl having 1 to 3 carbon atoms and A represents a divalent alkanediyl radical which has 1 to 4 carbon atoms and which is monosubstituted to hexasubstituted by identical or different substituents selected from the group consisting of fluorine, chlorine and bromine.

4. A 2-cyanobenzimidazole of the formula (I) according to claim 1, in which

R¹ represents hydrogen, chlorine, bromine, methyl or ethyl,

R² represents hydrogen, chlorine, bromine, methyl or ethyl and

A represents methylene, ethylene, propylene or butylene, each of which is monosubstituted to tetrasubstituted by identical or different substituents selected from the group consisting of fluorine, chlorine and bromine.

5. A 2-cyanobenzimidazole of the formula I, according to claim 1, in which

R¹ represents hydrogen,

R² represents hydrogen,

A represents methylene, ethylene, or propylene, each of which is monosubstituted to tetrasubstituted by identical or different substituents selected from the group consisting of fluorine or chlorine.

6. The 2-cyanobenzimidazoles represented by the following structural formulae:

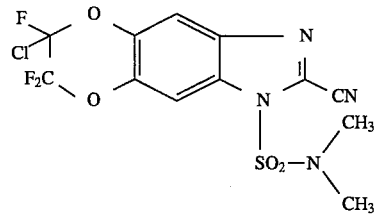

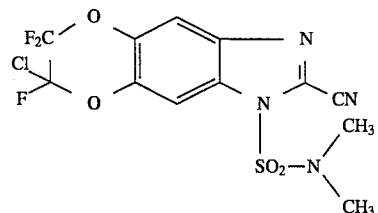

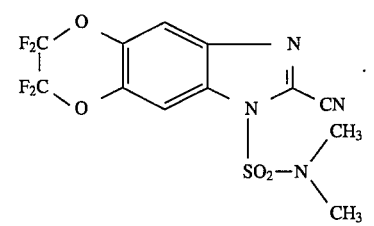

7. A 2-cyanobenzimidazole of the formula

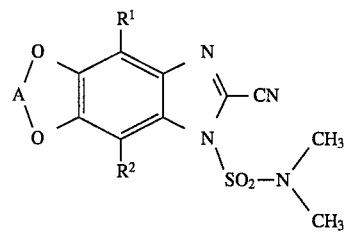

wherein A represents —$CF_2$—, R¹ represents H, and R² represents H.

8. A fungicidal arthropodicidal or nematocidal composition comprising an effective amount of a 2-cyanobenzimidazole of the formula (I) according to claim 1 and a suitable extender.

9. A method of combating fungi, arthropods and nematodes which comprises applying to such fungi, arthropods and nematodes or to a habitat thereof an effective amount of a 2-cyanobenzimidazole of the formula (I) according to claim 1.

10. A 2-cyanobenzimidazole which is unsubstituted in the 1-position, of the formula (II)

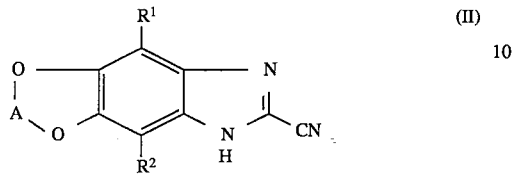

in which

R$^1$ represents hydrogen, halogen or alkyl,

R$^2$ represents hydrogen, halogen or alkyl and

A represents a divalent alkanediyl radical which has 1 to 4 carbon atoms and which is optionally monosubstituted or polysubstituted by identical or different substituents wherein the substituents are halogen, straight-chain or branched alkyl having 1 to 6 carbon atoms, straight-chain or branched halogenoalkyl having 1 to 6 carbon atoms and 1 to 13 identical or different halogen atoms, or a divalent alkanediyl radical having 3 to 7 carbon atoms.

* * * * *